United States Patent [19]

Okuyama et al.

[11] Patent Number: 5,496,829
[45] Date of Patent: Mar. 5, 1996

[54] USE OF 2-NITROXYETHYL (+)APOVINCAMINATE

[75] Inventors: Shigeru Okuyama; Susumu Otomo; Yutaka Kawashima; Katsuo Hatayama, all of Tokyo, Japan

[73] Assignee: Taisho Pharmaceutical Co., Ltd., Japan

[21] Appl. No.: 244,330

[22] PCT Filed: Dec. 8, 1992

[86] PCT No.: PCT/JP94/01601

§ 371 Date: May 24, 1994

§ 102(e) Date: May 24, 1994

[87] PCT Pub. No.: WO93/11765

PCT Pub. Date: Jun. 24, 1993

[30] Foreign Application Priority Data

Dec. 10, 1991 [JP] Japan .................................. 3-324932
Dec. 10, 1991 [JP] Japan .................................. 3-325445

[51] Int. Cl.$^6$ ........................................ A61K 31/44
[52] U.S. Cl. ......................................... 514/283
[58] Field of Search ................................ 514/283

[56] References Cited

U.S. PATENT DOCUMENTS 4,980,474  12/1990  Hayashi et al. ............................ 546/51

FOREIGN PATENT DOCUMENTS 2167279  6/1990  Japan .

OTHER PUBLICATIONS

65th Meeting of the Japanese Pharmacological Society, Mar. 22–25, 1992 & JPN J Pharmacol, vol. 59, Suppl. 1, p. 404p, 1992.
65th Annual Meeting of the Japanese Pharmacological Soc., Mar. 22–25, 1992 & JPN J Pharmacol, Col. 59, Suppl. 1, p. 309p, 1992.
Database WPI, Week 8713 AN87–088614 (1987).
Patent Abstracts of Japan, vol. 15, No. 461, (C–887) (4989) 22 Nov. 1991.
Patent Abstracts of Japan, vol. 14, No. 403, (C–753) (4346) 31 Aug. 1990.
Drug Dev. Res., 1988, vol. 14, pp. 335–341, Saekadi, Adam et al.
Eur J Phamacol (Netherlands) 23 Oct. 1990, vol. 187, No. 3 pp. 537–539, Gaal et al.
Yakuri to Chiryo, 1987, vol. 15, pp. 3643–3649.
Res Commun Chem Pathol Pharmacol (United States) Oct. 1993, vol. 82, No. 1, pp. 91–100.
66th Annual Meeting of the Japanese Pharmacological Soc., Mar. 24–27, 1993, vol. 61, Suppl. 1, p. 184P, 1993.

*Primary Examiner*—Kimberly R. Jordan
*Attorney, Agent, or Firm*—Lorusso & Loud

[57] ABSTRACT

2-nitroxyethyl (+)apovincaminate is used as an agent for relieving disturbance of consciousness and as a narcotic antagonist.

3 Claims, No Drawings

USE OF 2-NITROXYETHYL (+)APOVINCAMINATE

This application is a 371 of PCT/JP94/01601 filed Dec. 8, 1992.

TECHNICAL FIELD

The present invention relates to an agent for relieving disturbance of consciousness and a narcotic antagonist which contain 2-nitroxyethyl (+)apovincaminate (hereinafter referred to as VA-045) as an active ingredient.

BACKGROUND ART

In general, a central nervous mechanism which maintains and controls consciousness is composed of two systems, i.e., ascending midbrain reticular formation activating system and hypothalamus activating system. That is, brainstem reticular body and hypothalamus, as well as hemicerebrum and thalamus which are affected by them, are related to consciousness. Disturbance of consciousness occurs when the functions of these organs are impaired by an impact on head (neurotrauma) or cerebral ischemia. Agents for relieving disturbance of consciousness act on central nervous systems concerned with consciousness, to exhibit a relieving effect. As such agents for relieving disturbance of consciousness, there have been known thyrotropin releasing hormone tartrate (hereinafter referred to as TRH), meclofenoxate hydrochloride, CDP-choline, etc.

The ascending midbrain reticular formation activating system participates greatly in a central nervous mechanism which controls sleep. Anesthesia by use of pentobarbital or the like is induction of sleep by inhibition of the aforesaid activating system. Narcotic antagonists act on the inhibited ascending midbrain reticular formation activating system to recover the function of the system. As the narcotic antagonists, there have been known methamphetamine hydrochloride, doxapram hydrochloride, TRH, etc. The above-mentioned conventional agents for relieving disturbance of consciousness and narcotic antagonists, however, are all different from apovincaminic acid skeleton.

On the other hand, VA-045 is a compound disclosed in Japanese Patent KOKAI No. 2-167279, and it has an excellent curative effect on cerebral ischemia, hypertension and the like because of its cerebro-vasodilation effect. However, of apovincaminic acid derivatives including this compound, none is known to have relieving effect on disturbance of consciousness or antagonistic effect on narcotism.

By the way, cerebro-vasodilators improve cerebral circulation by relaxation of cerebral smooth muscle, and drugs heretofore known as cerebro-vasodilators (e.g. vinpocetine, nifedipine, nicardipine verapamil) do not have relieving effect on disturbance of consciousness or antagonistic effect on narcotism.

An object of the present invention is to provide an agent for relieving disturbance of consciousness and a narcotic antagonist which are novel.

DISCLOSURE OF THE INVENTION

The present invention is an agent for relieving disturbance of consciousness which contains VA-045 as an active ingredient, and the present invention is a narcotic antagonist containing VA-045 as an active ingredient.

An administration route of VA-045 as an agent for relieving disturbance of consciousness includes, for example, parenteral and oral administrations. An administration route of VA-045 as narcotic antagonist is parenteral administration. The dosage form of VA-045 is an injection in the case of parenteral administration, and a form selected from tablets, granules, powders, capsules, syrups and suspensions in the case of oral administration. When VA-045 is used as an agent for relieving disturbance of consciousness, these dosage forms may be properly chosen depending on the condition and age of a patient and the purpose of treatment, though the most preferable pharmaceutical form is an injection. Preparations of various pharmaceutical forms can be prepared by conventional preparation methods (for example, the methods prescribed in the No. 12 revised Japanese Pharmacopoeia) by using conventional excipients (e.g. crystalline cellulose, starch, lactose or mannitol), binders [e.g. hydroxypropyl cellulose or polyvinyl pyrrolidone], lubricants (e.g. magnesium stearate or talc), disintegrators (e.g. calcium carboxymethyl cellulose), etc.

As to the dose of VA-045, VA-045 is administered to an adult at a dose of 0.1 to 20 mg (parenterally) or 1 to 200 mg (orally) per day in 1 to 3 portions. The dose may be properly varied depending on the age, weight and condition of a patient.

BEST MODE FOR CARRYING OUT THE INVENTION

The present invention is illustrated below in further detail with reference to examples.

EXAMPLE 1

100 Grams of VA-045, 460 g of lactose, 300 g of corn starch, 100 g of calcium carboxymethyl cellulose and 30 g of a polyvinyl pyrrolidone were thoroughly mixed, granulated with ethanol by a conventional method, and dried, followed by particle size regulation. 10 Grams of magnesium stearate was added to the thus obtained granules and mixed therewith, after which the resulting mixture was made into tablets each with a weight of 100 mg by a conventional method.

EXAMPLE 2

A powder containing 10% of VA-045 was prepared by mixing 100 g of VA-045, 500 g of mannitol and 380 g of corn starch thoroughly, adding thereto 200 g of a 10% aqueous hydroxypropyl cellulose solution, granulating the resulting mixture, drying the granules, and then sieving the same by use of a No. 32 screen.

EXAMPLE 3

An injection was prepared by dissolving 1 mg of VA-045, 25 mg of a buffer and 11 mg of sodium chloride in 2 ml of distilled water for injection, filtering the resulting solution, dispensing the filtrate into 2 ml ampuls, sealing up the same therein, and then sterilizing the same.

INDUSTRIAL APPLICABILITY

As is clear from the test examples hereinafter described, the compound according to the present invention is useful because it has an excellent curative effect on disturbance of consciousness caused by an impact on head, cerebral ischemia or the like and is markedly effective as an antagonist against delay in awakening from narcosis after general anethesia or after anethesia of a corpulent person or an old person. Furthermore, the effects of the compound according to the present invention are long-acting effects and hence desirable.

The present invention is illustrated below in further detail with reference to test examples.

Test Example 1

Test for effect on disturbance of consciousness of a rat induced by an impact on the head In the test, male Wistar strain rats (body weight: 350 to 400 g) of 10- to 11-week-old were used and they were divided into groups of 10 to 12 rats each. A metal block of 400 g was dropped onto each rat in each group from a height of 70 cm to inflict a cephalic trauma [Journal of Neurotrauma, vol. 7, pp. 131–139 (1990)].

VA-045 was administered to each rat in each group intravenously in the tail at a dose of 0.1, 0.3 or 1.0 mg/kg in the form of a solution in 2.5% ascorbic acid immediately before the infliction of the cephalic trauma. As a reference drug, TRH was administered at a dose of 0.3, 1.0 or 3.0 mg/kg in the form of a solution in physiological saline in the same manner as above. In addition, groups to which a 2.5% ascorbic acid solution or physiological saline had been administered alone were used as controls.

For the rats in the above groups, the time required for the recovery of righting reflex after its loss and the time required for the recovery of spontaneous movement were measured, and unconsciousness time was defined as the interval between the recovery of righting reflex and the recovery of spontaneous movement. On the basis of the experimental results, the significant differences among the groups were determined by one-way analysis of variance and Dunnett's test. The results are shown in Table 1.

TABLE 1

| Dose | Unconsciousness time (sec.) |
|---|---|
| (control) | 1118.42 ± 178.84 |
| VA-045 0.1 mg/kg | 458.70 ± 109.10* |
| VA-045 0.3 mg/kg | 120.36 ± 18.63** |
| VA-045 1.0 mg/kg | 60.20 ± 24.26** |
| (control) | 921.83 ± 121.26 |
| TRH 0.3 mg/kg | 572.8 ± 108.61 |
| TRH 1.0 mg/kg | 399.90 ± 88.58** |
| TRH 3.0 mg/kg | 86.40 ± 23.22** |

*: $p < 0.05$
**: $p < 0.01$ (Dunnett's test)

Like TRH, VA-045 reduced the unconsciousness time in a dose-dependent manner, namely, it had a significant relieving effect.

Test Example 2

Test for effect on disturbance of consciousness of a mouse induced by an impact on the head In the test, male ICR strain mice (25 to 35 g) of 4- to 5-week-old were used and they were divided into groups of 8 to 15 mice each. A Bakelite column of 21 g was dropped onto each mouse in each group to inflict a cephalic trauma [Naunyn-Schmiedeberg's Archives of Pharmacology, vol. 336, pp. 561–565 (1987)]

VA-045 was administered to each mouse in each group intravenously in the tail at a dose of 0.03, 0.1 or 0.3 mg/kg in the form of a solution in 2.5% ascorbic acid 10 minutes before the infliction of the cephalic trauma. As a reference drug, TRH was administered at a dose of 0.1, 0.3 or 1.0 mg/kg in the form of a solution in physiological saline in the same manner as above. In addition, groups to which a 2.5% ascorbic acid solution or physiological saline had been administered alone were used as controls.

For the mice in the above groups, the time required for the recovery of righting reflex after its loss and the time required for the recovery of spontaneous movement were measured, and unconsciousness time was defined as the interval between the recovery of righting reflex and the recovery of spontaneous movement. On the basis of the experimental results, the significant differences among the groups were determined by one-way analysis of variance and Dunnett's test. The results are shown in Table 2.

TABLE 2

| Dose | Unconsciousness time (sec.) |
|---|---|
| (control) | 193.5 ± 29.5 |
| VA-045 0.03 mg/kg | 111.6 ± 27.9* |
| VA-045 0.1 mg/kg | 48.4 ± 34.1** |
| VA-045 0.3 mg/kg | 19.7 ± 10.8** |
| (control) | 329.1 ± 80.8 |
| TRH 0.3 mg/kg | 273.8 ± 60.3 |
| TRH 1.0 mg/kg | 106.1 ± 23.0* |
| TRH 3.0 mg/kg | 123.4 ± 27.4 |

*: $p < 0.05$
**: $p < 0.01$ (Dunnett's test)

Like TRH, VA-045 reduced the unconsciousness time in a dose-dependent manner, namely, it had a significant relieving effect.

Test Example 3

Test for effect on disturbance of consciousness of a rat induced by cerebral ischemia In the test, male Wistar strain rats (body weight: 250 to 300 g) of 10-week-old were used and they were divided into groups of 5 to 11 rats each. Complete cerebral ischemia was caused by occluding the vertebral artery on both sides and then occluding the common carotid artery for 10 minutes on both sides [Stroke, vol. 10, pp. 267–272 (1979)]

VA-045 was administered to each rat in each group intraperitoneally at a dose of 0.3, 1.0 or 3.0 mg/kg in the form of a suspension in 5% gum arabic immediately before opening the common carotid artery. As a reference drug, TRH was administered at a dose of 1.0, 3.0 or 10 mg/kg in the form of a solution in physiological saline in the same manner as above. As a cerebro-vasodilator, vinpocetine [Pharmacology and Therapy, vol. 10, pp. 1877–1890 (1982)] was administered at a dose of 1.0, 3.0 or 10 mg/kg in the form of a suspension in 5% gum arabic in the same manner as above. In addition, groups to which 5% gum arabic or physiological saline had been administered alone were used as controls.

For the rats in the above groups, the time required for the recovery of righting reflex after its loss by the occlusion of the common carotid artery and the time required for the recovery of spontaneous movement were measured, and unconsciousness time was defined as the interval between the recoveries. On the basis of the experimental results, the significant differences among the groups were determined by one-way analysis of variance and Dunnett's test. The results are shown in Table 3.

TABLE 3

| Dose | Unconsciousness time (sec.) |
|---|---|
| (control) | 3386.8 ± 422.6 |
| VA-045 0.3 mg/kg | 2448.2 ± 303.5 |
| VA-045 1.0 mg/kg | 2022.3 ± 224.4* |
| VA-045 3.0 mg/kg | 1516.5 ± 163.3** |
| (control) | 2886.0 ± 333.6 |
| TRH 1.0 mg/kg | 1887.8 ± 136.5* |
| TRH 3.0 mg/kg | 1628.3 ± 155.3** |
| TRH 10 mg/kg | 1655.0 ± 267.6* |
| (control) | 2605.1 ± 297.6 |
| vinpocetine 1.0 mg/kg | 2494.4 ± 150.2 |
| vinpocetine 3.0 mg/kg | 2745.1 ± 337.6 |
| vinpocetine 10 mg/kg | 2190.4 ± 317.1 |

*: $p < 0.05$
**: $p < 0.01$ (Dunnett's test)

Like TRH, VA-045 reduced the unconsciousness time in a dose-dependent manner, namely, it had a significant relieving effect. On the other hand, vinpocetine, a cerebro-vasodilator was ineffective.

Test Example 4

Effect on pentobarbital anesthesia of a rat

In the experiment, male Wistar strain rats (250 to 300 g) of 10-week-old were used and they were divided into groups of 10 rats each. Pentobarbial sodium (50 mg/kg) was intraperitoneally administered to each rat in each group to induce sleep [Life Sciences, vol. 14, pp. 447–455 (1974)].

VA-045 was administered to each rat in each group intravenously in the tail at a dose of 0.1, 0.3 or 1.0 mg/kg in the form of a solution in 2.5% ascorbic acid 10 minutes after the administration of pentobarbital sodium. As a reference drug, TRH was administered at a dose of 1.0, 3.0 or 10.0 mg/kg in the form of a solution in physiological saline in the same manner as above. In addition, groups to which a 2.5% ascorbic acid solution or physiological saline had been administered alone were used as controls.

For the rats in the above groups, the sleeping time was measured. On the basis of the experimental results, the significant differences among the groups were determined by one-way analysis of variance and Dunnett's test. The results are shown in Table 4.

TABLE 4

| Dose | Sleeping time (sec.) |
|---|---|
| (control) | 5378.25 ± 225.85 |
| VA-045 0.1 mg/kg | 4750.62 ± 280.01 |
| VA-045 0.3 mg/kg | 3742.87 ± 227.18** |
| VA-045 1.0 mg/kg | 3418.75 ± 117.51** |
| (control) | 4923.12 ± 559.64 |
| TRH 1.0 mg/kg | 4108.63 ± 355.79 |
| TRH 3.0 mg/kg | 3639.00 ± 348.49 |
| TRH 10 mg/kg | 3036.63 ± 173.66** |

**: $p < 0.01$ (Dunnett's test)

Like TRH, VA-045 reduced the sleep introduced by pentobarbital, in a dose-dependent manner, namely, it had a significant relieving effect.

Test Example 5

Effect on pentobarbital anesthesia of a rabbit

In the experiment, male Japanese white rabbits (2.5 to 3.0 kg) were used and they were divided into groups of 8 rabbits each. Sleep was induced by intravenous administration of pentobarbial sodium (30 mg/kg).

VA-045 was administered to each rabbit in each group intravenously in the ear at a dose of 0.1, 0.3 or 1.0 mg/kg in the form of a solution in 2.5% ascorbic acid 10 minutes after the administration of pentobarbital sodium. As a reference drug, TRH was administered in a dose of 0.3, 1.0 or 3.0 mg/kg in the form of a solution in physiological saline in the same manner as above. In addition, groups to which a 2.5% ascorbic acid solution or physiological saline had been administered alone were used as controls.

For the rabbits in the above groups, the sleeping time was measured. On the basis of the experimental results, the significant differences among the groups were determined by one-way analysis of variance and Dunnett's test. The results are shown in Table 5.

TABLE 5

| Dose | Sleeping time (sec.) |
|---|---|
| (control) | 3342.54 ± 511.22 |
| VA-045 0.1 mg/kg | 2723.41 ± 231.02 |
| VA-045 0.3 mg/kg | 2310.14 ± 200.22** |
| VA-045 1.0 mg/kg | 1789.63 ± 164.11** |
| (control) | 2334.77 ± 210.11 |
| TRH 0.3 mg/kg | 2219.55 ± 389.72 |
| TRH 1.0 mg/kg | 2232.12 ± 221.46 |
| TRH 3.0 mg/kg | 2209.83 ± 192.14 |

*: $p < 0.05$
**: $p < 0.01$ (Dunnett's test)

VA-045 reduced the sleep introduced by pentobarbital, in a dose-dependent manner, namely, it had a significant relieving effect. TRH had no relieving effect.

Test Example 6

Acute toxicity test

Wistar strain rats (7-week-old) were divided into groups each consisting of 5 male rats and 5 female rats. Each of solutions of VA-045 in 10% ascorbic acid having various concentrations was administered to them intravenously or orally, and dead rats were counted by observation for 2 weeks. Consequently, in the case of the intravenous administration, no rat died by administration of VA-045 at a dose of 16.9 mg/kg and $LD_{50}$ value was judged to be 21.4 mg/kg.

On the other hand, in the case of the oral administration, $LD_{50}$ value was judged to be 2000 mg/kg or more.

We claim:

1. A method for treating disturbance of consciousness which comprises administering an effective amount of 2-nitroxyethyl (+)apovincaminate to a patient.

2. A method in accordance with claim 1 wherein said disturbance of conciousness is caused by neurotrauma to the head or cerebral ischemia.

3. A method for accelerating awakening from narcosis after general anesthesia in a patient, which comprises administering an effective amount of 2-nitroxyethyl (+) apovincaminate to the patient.

* * * * *